(12) United States Patent
Belk et al.

(10) Patent No.: US 10,399,707 B2
(45) Date of Patent: Sep. 3, 2019

(54) NANO-ENERGETIC APPLICATIONS FOR AIRCRAFT

(71) Applicant: THE BOEING COMPANY, Chicago, IL (US)

(72) Inventors: John H. Belk, Chicago, IL (US); Om Prakash, Bangalore (IN)

(73) Assignee: The Boeing Company, Chicago, IL (US)

(*) Notice: Subject to any disclaimer, the term of this patent is extended or adjusted under 35 U.S.C. 154(b) by 227 days.

(21) Appl. No.: 15/379,301

(22) Filed: Dec. 14, 2016

(65) Prior Publication Data

US 2018/0162556 A1    Jun. 14, 2018

(51) Int. Cl.
| | | |
|---|---|---|
| *B64F 5/60* | (2017.01) | |
| *B64D 15/16* | (2006.01) | |
| *H02N 10/00* | (2006.01) | |
| *G01N 29/34* | (2006.01) | |
| *G01N 29/24* | (2006.01) | |
| *C06B 33/00* | (2006.01) | |
| *G01N 29/04* | (2006.01) | |
| *G01N 29/44* | (2006.01) | |
| *G01N 29/46* | (2006.01) | |
| *E01H 8/02* | (2006.01) | |

(52) U.S. Cl.
CPC ............ *B64F 5/60* (2017.01); *B64D 15/16* (2013.01); *C06B 33/00* (2013.01); *G01N 29/045* (2013.01); *G01N 29/2431* (2013.01); *G01N 29/2437* (2013.01); *G01N 29/348* (2013.01); *G01N 29/4436* (2013.01); *G01N 29/4472* (2013.01); *G01N 29/46* (2013.01); *H02N 10/00* (2013.01); *E01H 8/02* (2013.01); *G01N 2291/0289* (2013.01); *G01N 2291/2694* (2013.01)

(58) Field of Classification Search
CPC ...... B64D 15/16; C06B 33/00; G01N 29/043; G01N 29/07
USPC .......................................................... 73/594
See application file for complete search history.

(56) References Cited

U.S. PATENT DOCUMENTS

| | | | | |
|---|---|---|---|---|
| 8,447,530 B2* | 5/2013 | Pado | ...................... | G01M 7/025 702/36 |
| 2010/0005896 A1* | 1/2010 | Miller | ................. | B29C 65/8284 73/779 |

(Continued)

*Primary Examiner* — Tarun Sinha
(74) *Attorney, Agent, or Firm* — Haynes and Boone LLP

(57) ABSTRACT

A non-destructive examination (NDE) system for use on a structural element comprises nano-energetic actuators configured for creating a controlled combustion in response to thermal energy, thereby inducing vibrations in a surface of the structural element. The NDE system further comprises sensors configured for measuring the vibrations induced in the surface of the structural element and generating vibration data. An applique comprises a planar substrate, nano-energetic actuators affixed to the planar substrate, each configured for creating controlled combustions in response to thermal energy, and an adhesive affixed to the planar substrate, such that the applique can be adhered to a structural element. A means of transportation having an accumulation of ice comprises a structural element, and nano-energetic actuators, each configured for creating a controlled combustion in response to thermal energy, thereby inducing vibrations in a surface of the structural element great enough to generate cracks in the ice.

21 Claims, 10 Drawing Sheets

(56) References Cited

U.S. PATENT DOCUMENTS

| | | | |
|---|---|---|---|
| 2010/0013352 A1* | 1/2010 | Pletner | F16F 15/005 |
| | | | 310/316.01 |
| 2013/0173181 A1* | 7/2013 | Shaikh | G01N 29/14 |
| | | | 702/34 |
| 2014/0123761 A1* | 5/2014 | Turner | G01N 29/11 |
| | | | 73/628 |

* cited by examiner

NANO-ENERGETIC APPLICATIONS FOR AIRCRAFT

FIELD

The present disclosure generally relates to techniques for monitoring and/or facilitating the safety of vehicles, and more particularly, to non-destructive examination (NDE) and de-icing techniques used on structural bodies, such as those found in aircraft.

BACKGROUND

Currently, inspection for damage or deterioration to structural bodies (e.g., aircraft composite structures) due to fatigue or impacts must be performed on a fixed schedule. These inspections are done to assess the integrity of the structure in question. Each inspection is time-consuming and is costly, not only in terms of time and skill needed to perform a thorough job, but also in terms of lost revenue from the structural bodies (e.g., aircraft) being out-of-service. Inspection of structural bodies is typically performed using what is referred to as "Non-Destructive Evaluation (NDE)," which requires careful location of multiple transducers (both actuating and sensing) on the structural body to provide for a fairly high energy path during transducer-to-transducer energy transfer.

In the case of aircraft, an automated on-board system may be designed to perform NDE, thereby eliminating the cost of potentially lost revenue from out-of-service aircraft, except when significant damage has actually occurred. In addition, because the damage has been located and/or characterized (e.g., determination of damage size, depth, etc.), repairs can be performed more quickly by using appropriate repair kits. Such an on-board system may include actuators and sensors in the form of transducers that are typically large, expensive, and require individual wiring. In certain applications, the additional weight of the wiring and/or the transducers may be prohibitive, especially for aircraft. Conventional wiring is also very heavy and requires a large amount of manual labor to install. In addition, the cost of a large number of transducers applied over a large area may be prohibitive. Another drawback to the use of large known transducers is that the signal-to-noise ratio for the long paths between the actuators and sensor is much lower than that of shorter paths. Long paths make it difficult to localize and determine the shape of a damage site.

To address these concerns, a lightweight scalable transducer system that allows the assessment of the integrity of a structural body in real-time or near real-time has been developed, as described in U.S. Pat. No. 8,447,530, which is expressly incorporated herein by reference. This lightweight scalable transducer system uses actuators, e.g., in the form of relatively inexpensive piezoelectric transducers (PZTs). The advent of direct write electronics and other additive manufacturing processes make the approach described in U.S. Pat. No. 8,447,530 more economically viable and brings possibilities of Active Damage Interrogation (ADI) during flight or ground operations. However, even with direct write of the transducers and electronics, this requires the part surface to be available for application of the wiring and materials and is best suited for investment in this at the time of manufacture of the structure.

Furthermore, it is desirable to maximize the sensitivity of an NDE system to damage or degradation of a structure by generating as much energy from the actuators in an NDE system as possible in order to provide a "clean" signal that will traverse all discontinuities in the structure. The use of relatively small and inexpensive PZT actuators in an NDE system may be fine up to a point, but these PZT actuators might not always generate enough energy to provide the desired signals. The relatively low energy signals may be integrated over time; however, this technique may extend the time to interrogate the structure longer than desired. In some scenarios, such as when the aircraft is on the ground, the structure may be hit with a rubber mallet in order to generate a relatively high energy signal that can then be sensed by the sensors of the NDE system. However, this technique cannot be performed in-flight, and cannot be routinely performed at inaccessible locations of the structure without disassembling the structure.

There, thus, remains a need for a relatively inexpensive, light-weight, and high energy transducer for use in an NDE system for monitoring of damage or deterioration in structures, such as aircraft structures.

Another issue that arises in the context of airplane flight is the accumulation of ice on leading edges of the wings and flight control surfaces, which may ultimately lead to loss of control or insufficient lift to keep the aircraft airborne, as well as the accumulation of ice on sensors, transducers, and probes, which may lead to erroneous data readings, and therefore, a potentially deleterious effect on the functioning of the aircraft. Electric deicing heaters, may be used to melt, and therefore prevent dangerous build up, of ice, on the critical components exposed to the external environment. However, this may take an extended period of time, causing scheduling delays in flights, especially if the ice is relatively thick.

There, thus, remains a need for a more efficient means to remove ice from aircraft.

SUMMARY

In accordance with one aspect of the present inventions, a non-destructive examination (NDE) system for use on a structural element comprises is provided. The NDE system comprise at least one nano-energetic actuator, each configured for creating a controlled combustion in response to thermal energy, thereby inducing vibrations in a surface of the structural element. The NDE system may optionally comprises at least one ignition element configured for generating the thermal energy in response to at least one electrical pulse, and at least one energy source configured for generating at least one electrical pulse. In one embodiment, each of the nano-energetic actuator(s) comprises copper oxide, and each of the ignition element(s) comprises platinum. Each of the nano-energetic actuator(s) may comprise nano-energetic material having a particle size less than 100 nanometers, and may have a size in the range of 1 micrometer to four millimeters.

The NDE system further comprises at least one sensor configured for measuring the vibrations induced in the surface of the structural element and generating vibration data. In one embodiment, the NDE system further comprises a data collection device configured for collecting and storing the vibration data, and at least one processor configured for determining a condition of the structural element based on the collected and stored vibration data. If multiple nano-energetic actuators are provided, the NDE system may further comprise a processor programmed to control delivery of a plurality of electrical pulses from the at least one electrical source to cause the plurality of nano-energetic actuators to generate a plurality of controlled combustions in a time-phased manner. The NDE system optionally comprises at least one electro-mechanical transducer, each configured for vibrating in response to at least one electrical pulse, thereby inducing vibrations in the surface of the structural element.

In accordance with a second aspect of the present inventions, a means of transportation is provided. The means of transportation comprises a structural element (e.g., a bridge, railroad, or vehicular structural element, such as the structural element of an aircraft).

In accordance with a third aspect of the present inventions, a method of performing a non-destructive examination (NDE) on a structural element (e.g., a bridge, railroad, or vehicular structural element, such as the structural element of an aircraft) is provided. The method comprises applying at least one controlled combustion to the structural element, thereby inducing vibrations in the structural element. In one method, the controlled combustion(s) does not damage the structural element. If the structural element is a structural element of an aircraft, the controlled combustion(s) can be applied to the aircraft structural element in-flight. In one method, a plurality of controlled combustions is applied to the structural element in a time-phased manner to preferentially induce the vibrations along a particular direction in the structural element.

The method further comprises measuring the vibrations induced in the surface of the structural element, generating vibration data corresponding the measured vibrations, collecting and storing the vibration data, and determining a condition of the structural element based on the collected and stored vibration data.

In accordance with a fourth aspect of the present inventions, an applique comprises a planar substrate (e.g., one composed of a polymeric material, metallic foil, a metalized polymeric material, or a multilayer substrate of polymeric and metallic films), and a plurality of nano-energetic actuators affixed to the planar substrate, each configured for creating a plurality of controlled combustions in response to thermal energy. Each of the nano-energetic actuators may comprise nano-energetic material (e.g., copper oxide) having, e.g., a particle size less than one hundred nanometers, and may have a size, e.g., in the range of one micrometer to four millimeters.

The applique further comprises an adhesive affixed to the planar substrate, such that the applique can be adhered to a structural element. The applique may optionally comprise a plurality of ignition elements (e.g., platinum), at least one inductive coil, and a plurality of electrically conductive interconnections affixed to the planar substrate. The ignition elements are thermally coupled to the nano-energetic actuators, and the electrically conductive connections electrically couple the inductive coil(s) to the ignition elements.

In one embodiment, the applique further comprises a plurality of sensors, at least one data collection device, and at least one processor affixed to the planar substrate. The sensors are configured for measuring vibrations induced in the surface of the structural element by the plurality of controlled combustions, and generating vibration data, the data collection device(s) is configured for collecting and storing the vibration data, and the processor(s) is programmed to control delivery of a plurality of electrical pulses from an electrical source to the plurality of ignition elements to cause the plurality of nano-energetic actuators to generate the plurality of controlled combustions in a time-phased manner.

In accordance with a fifth aspect of the present invention, a method of manufacturing an applique is provided. The method comprises providing a planar substrate (e.g., one composed of a polymeric material, metallic foil, a metalized polymeric material, or a multilayer substrate of polymeric and metallic films). The method further comprises depositing a plurality of nano-energetic actuators on the planar substrate, each configured for creating a plurality of controlled combustions in response to thermal energy. Each of the nano-energetic actuators may comprise nano-energetic material (e.g., copper oxide) having, e.g., a particle size less than one hundred nanometers, and may have a size, e.g., in the range of one micrometer to four millimeters. The method further comprises affixing an adhesive to the planar substrate, such that the applique can be adhered to a structural element.

One method further comprises depositing a plurality of ignition elements (e.g., platinum) on the planar substrate, such that the plurality of ignition elements is thermally coupled to the plurality of nano-energetic actuators, depositing at least one inductive coil disposed on the planar substrate, such that the at least one inductive coil is electrically coupled to the plurality of ignition elements, and depositing a plurality of electrically conductive interconnections on the planar substrate, such that the plurality of electrically conductive interconnections electrically couple the at least one inductive coil to the nano-energetic actuators.

Another method further comprises depositing a plurality of sensors, at least one data collection device, and at least one processor on the planar substrate. The plurality of sensors are configured for measuring vibrations induced in the surface of the structural element by the plurality of controlled combustions, and generating vibration data, the data collection device(s) is configured for collecting and storing the vibration data, and the processor(s) is programmed to control delivery of a plurality of electrical pulses from an electrical source to the plurality of ignition elements to cause the plurality of nano-energetic actuators to generate the plurality of controlled combustions in a time-phased manner.

In accordance with a sixth aspect of the present inventions, a method of removing ice from a structural element (e.g., a bridge, railroad, or vehicular structural element, such as the structural element (e.g., a wing or flight control surface) of an aircraft) is provided. The method comprises applying at least one controlled combustion to the structural element adjacent the ice, thereby inducing vibrations in a surface of the structural element, such that cracks are formed in the ice, and optionally applying vibrations to the cracked ice via electro-mechanical actuators, thereby removing the cracked ice from the structural element. The controlled combustion(s) preferably does not damage the structural element. In one method, controlled combustions may be generated in a time-phased manner to induce the vibrations in the surface of the structural element.

In accordance with a seventh aspect of the present inventions, a means of transportation having an accumulation of ice is provided. The means of transportation comprises a structural element (e.g., a bridge, railroad, or vehicular structural element, such as the structural element (e.g., a wing or flight control surface) of an aircraft), and at least one nano-energetic actuator, each configured for creating a controlled combustion in response to thermal energy, thereby inducing vibrations in a surface of the structural element great enough to generate cracks in the ice. The means of transportation may optionally comprise at least one electro-mechanical transducer, each configured for vibrating in response to the at least one electrical pulse, thereby inducing vibrations in the surface of the structural element great enough to remove the cracked ice from the structural element.

The means of transportation may optionally comprises at least one ignition element configured for generating the thermal energy in response to at least one electrical pulse, and at least one energy source configured for generating at least one electrical pulse. In one embodiment, each of the nano-energetic actuator(s) comprises copper oxide, and each of the ignition element(s) comprises platinum. Each of the nano-energetic actuator(s) may comprise nano-energetic material having a particle size less than 100 nanometers, and may have a size in the range of 1 micrometer to four millimeters. If multiple nano-energetic actuators are provided, the means of transportation may further comprise a processor programmed to control delivery of a plurality of electrical pulses from the at least one electrical source to cause the plurality of nano-energetic actuators to generate a plurality of controlled combustions in a time-phased manner.

Other and further aspects and features of the invention will be evident from reading the following detailed description of the preferred embodiments, which are intended to illustrate, not limit, the invention.

BRIEF DESCRIPTION OF DRAWINGS

The drawings illustrate the design and utility of preferred embodiments of the present inventions, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

Figure 1:
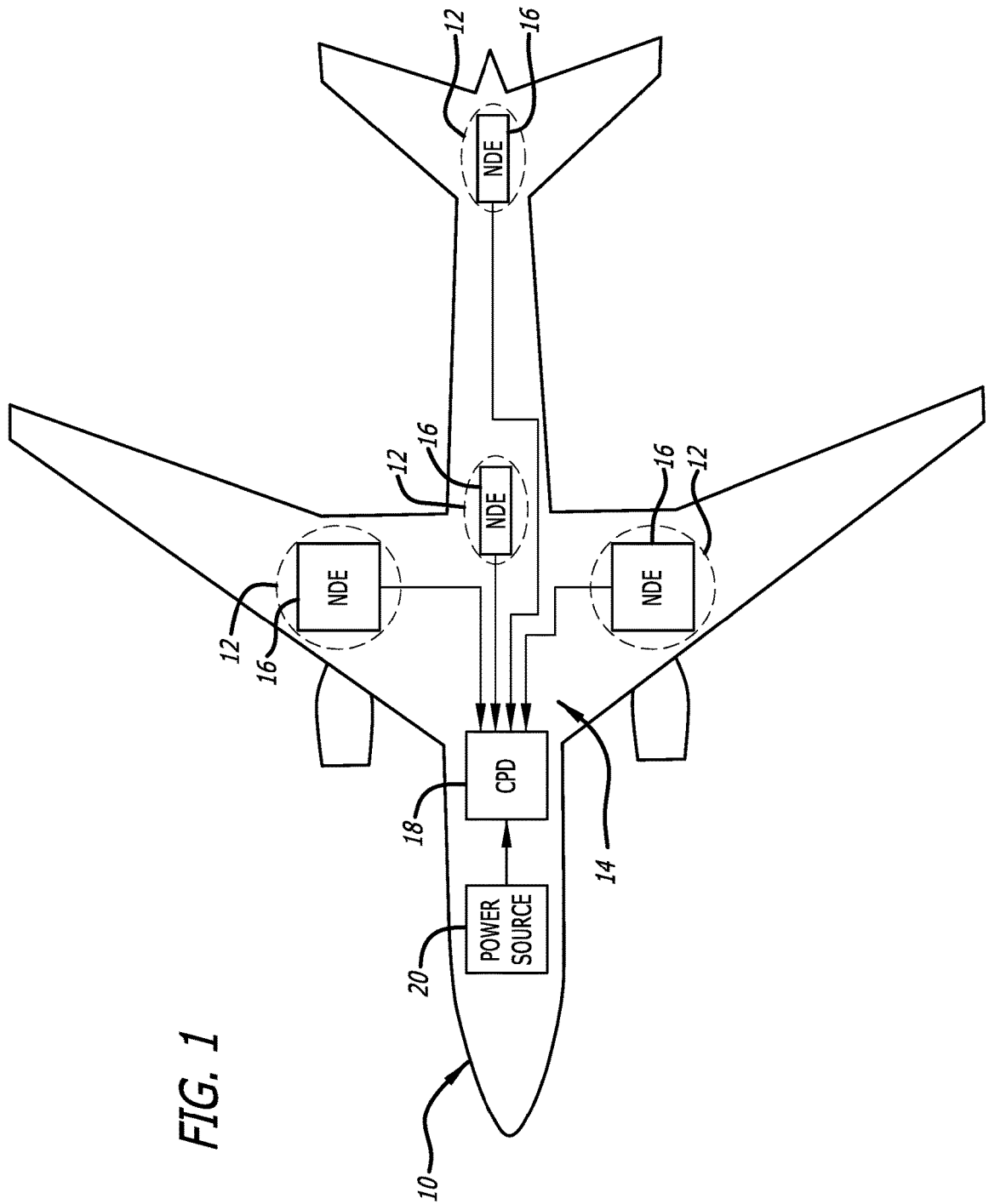
FIG. 1 is a block diagram of a Non-Destructive Evaluation (NDE) system constructed in accordance with one embodiment of the present inventions.

Referring to FIG. 1, a vehicle 10 constructed in accordance with one embodiment of the present inventions will now be described. The vehicle 10 may be an aircraft, a ground vehicle, a naval vessel or any other vehicle or structure requiring structural health monitoring. The vehicle 10 comprises structural elements 12, which may include, but is not limited to, a fuselage, door, panel, wing, engine component, or any other component that is susceptible to damage or deterioration. The structural elements 12 may include any material or combination of materials typically present in a conventional vehicle 10 or structure construction. For example, the structural elements 12 may include metal, composite, polymer, ceramic or any other material typically utilized for construction of vehicles 10 or other structures. Although FIG. 1 illustrates a vehicular structure element, and in particular an aircraft structural element, the present disclosure is not limited to vehicular structural elements and may include any other structural element associated with a means of transportation, e.g., bridges or railroads, or any structural element associated with other fixed structures, such as buildings, architectural elements, and other structures.

The vehicle 10 comprises a Non-Destructive Evaluation (NDE) system 14 configured for monitoring the health of the structural elements 12 of the vehicle 10. "Health monitoring", "structural health" and other uses of the term "health", as used herein include the structural integrity of a structure, component or equipment element. For example, damage to a surface or structure may include indentation, delamination (localized or otherwise), scratches, cracks, water soaking into material, or any other damage caused by impact or other contact. In addition, damage may include a reduction in the integrity of the structure that may require analysis and/or potential repair.

The NDE system 14 monitors the health of the structural elements 12 of the vehicle 10 by obtaining acoustic signatures between transmit and receive transducers affixed to each structural element 12. Such an acoustic signature provides a lot of information about the structural elements 12, which may be quite useful when using the structural elements 12 of the vehicle 10 beyond their designed life or designed performance. Presently acquired acoustic signatures can be compared to a baseline acoustic signature to ascertain whether the characteristics of the respective structural element 12 have changed in a manner that indicates damage or deterioration of the structural element 12.

To this end, the NDE system 14 generally comprises a plurality of damage monitoring units 16 respectively associated with the structural elements 12, a central processing device (CPD) 18 (which may be contained in an single integrated device or may be distributed amongst several components) in communication with each of the damage monitoring units 16 for determining and localizing any damage to deterioration in one of the structural elements 12, and a power source 20 configured for providing electrical power and signals to the damage monitoring units 16 and central processing device (CPD) 18. While FIG. 1 is shown as including four damage monitoring units 16, more or less than four damage monitoring units 16 may be present on the vehicle 10.

Significantly, the NDE system 14 is capable of injecting relatively high energy acoustic signals into each structural element 12 compared to prior art NDE systems without an increase in cost or weight. The NDE system 14 accomplishes this feat by utilizing nano-energetic material, instead of piezoelectric material, to generate the vibrational signal within each structural element 12.

Figure 2:
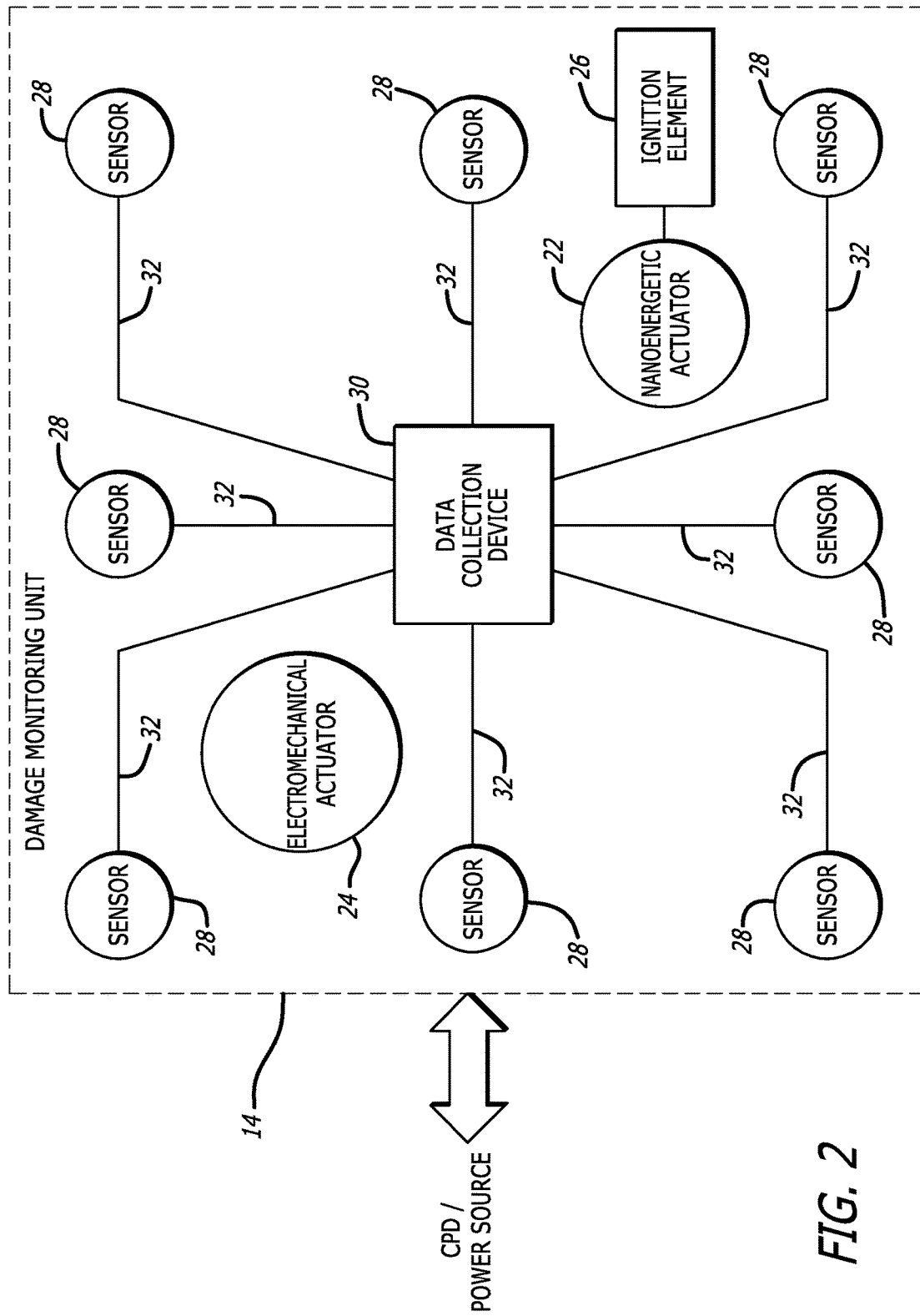
FIG. 2 is a block diagram of a representative damage monitoring unit used in the NDE system of FIG. 1.

To this end, and with reference to FIG. 2, each damage monitoring unit 16 comprises one or more nano-energetic actuators 22 (only one in the embodiment illustrated in FIG. 2), each of which is configured for creating a controlled combustion in response to thermal energy, thereby inducing vibrations in a surface of the respective structural element 12. Nano-energetic material can be defined as a metastable intermolecular composite (MIC) characterized by a particle size of its main constituents (a metal and a metal oxide) under one micron, and typically under one hundred nanometers. Nano-energetic material allows for high volumetric energy density, is capable of producing controlled combustion, may be environmentally benign, and allows for high and customizable reaction rates. In the illustrated embodiment, the nano-energetic material comprises an aluminum-copper (II) oxide, although the nano-energetic material may comprise, e.g., aluminum-molybdenum (VI) oxide, aluminum-iron (II, III) oxide, antimony-potassium permanganate, aluminum-potassium permanganate, aluminum-bismuth (III) oxide, aluminum-tungsten (VI) oxide hydrae, aluminum-fluoropolymer, or titanium-boron. Each nano-energetic actuator 22 may have a suitable size that induces the necessary vibrational energy in the surface of the structural element 12 without causing damage to the structural element 12, e.g., in the range of one micrometer to four millimeters.

Advantageously, the vibrational energy induced into the surface of the respective structural element 12 by the controlled combustion of the nano-energetic actuator 22 is substantially greater than the energy or energy per unit time that would otherwise be induced into the surface of the structural element 12 by a conventional piezoelectric transducer (PZT). However, such vibrational energy generated by the nano-energetic actuator 22 is substantially small enough, such that the structural element 12 is not damaged. Thus, the composition of the structural element 12 will preferably be taken into account when considering the size and composition of the nano-energetic actuator 22. For example, if the structural element 12 is composed of metal, the nano-energetic actuator 22 may be designed to generate a larger energy controlled combustion, and if the structural element 12 is composed of a ceramic or polymer material, the nano-energetic actuator 22 may be designed to generate a smaller energy controlled combustion.

It is preferable that the energy released by the nano-energetic actuator 22 be matched to the composition of the structural element 12 that is intended to interact with. In particular, it is desirable that the propagation of the vibration energy resulting from the controlled combustion of the nano-energetic actuator 22 be maximized within the structural element 12. Although the controlled combustion will generally produce a vibrational spike having broadband frequencies, not all of these frequencies will propagate through the structural element 12, especially one with discontinuities that will serve as a filter, allowing some frequencies to pass through, while preventing other frequencies from passing through. As such, the controlled combustion of the nano-energetic actuator 22 is preferably tuned to a natural resonant frequency of the structural element 12 to ensure that the vibrational energy propagates across these discontinuities. The natural resonant frequency to which the controlled combustion of the nano-energetic actuator 22 is tuned is preferably one that provides good transmission along the entire path and is within the frequency range of the sensors (described below).

Each damage monitoring unit 16 may additionally comprise one or more electro-mechanical actuators 24 (only one in the embodiment illustrated in FIG. 2) in the form of a PZT that, like the nano-energetic actuator 22, induces vibrations into the structural element 12. However, the vibrational energy provided by the electro-mechanical actuator 24 is substantially less than the vibration energy or energy per unit time provided by the nano-energetic actuator 22.

Each damage monitoring unit 16 optionally comprises one or more ignition elements 26 (only one in the embodiment illustrated in FIG. 2) configured for generating the thermal energy necessary for the nano-energetic actuator 22 to generate the controlled combustion. In the illustrated embodiment, the ignition element 26 takes the form of a thermoelectric transducer that is in physical contact with the nano-energetic actuator 22 and that generates the thermal energy in response to an electrical signal (e.g., a 5V pulse). The ignition element 26 may, e.g., be composed of well-known material used in conventional low-resistance electric igniters, e.g., platinum wire, to generate the thermal energy necessary to initiate the reaction in the nano-energetic actuator 22. Alternatively, the ignition elements may be electromagnetic energy—based, e.g., using a laser or flash light or radio frequency source, or friction-based, e.g., by impacting the nano-energetic actuator 22. In alternative embodiments, the simple application of a voltage may generate the thermal energy necessary for the nano-energetic actuator 22 to generate the controlled combustion, in which case, a separate ignition element may not be required.

Each damage monitoring unit 16 further comprises a plurality of sensors 28 that are configured for measuring the vibrations induced in the surface of the structural element 12 by the nano-energetic actuator 22 and optional electro-mechanical actuator 24, and generating electrical vibration data in response thereto. The sensors 28 may be any device capable of measuring vibration or other vibratory motion, such as, but not limited to, a transducer. Devices suitable for use as sensors 28 may include piezoelectric transducers (PZTs), accelerometers, strain gages, fiber optic sensors, and/or any other device that responds to a high frequency vibration. For example, a PZT may generate a measurable voltage in response to a sensed vibration. By "vibration," "vibratory motion," and grammatical variations thereof, as used herein, it is meant to include reciprocal or non-reciprocal motions and/or strain within a material that are capable of being sensed and/or measured at a distance across a material. Optical measurements of small distance measurement may also be used to sense vibration including those based on interferometry- or Moiré-based techniques.

Each damage monitoring unit 16 further comprises a data collection device 30 configured for collecting and storing the vibration data generated by the sensors 28 of the respective damage monitoring unit 16. The data collection device 30, may, e.g., be a microprocessor, integrated circuit or other device capable of collecting and/or analyzing data provided by the sensors 28. For example, while not being limited to particular parameters, the data collection device 30 may be a microprocessor or integrated circuit having the following parameters: at least about eight analog-to-digital (ND) conversion channels at 3 MHz each, about at least 1024 data points per channel; at least about 1 Kb memory storage per channel temporary, at least about 1 Kb memory storage per channel permanent, and sufficient memory to perform a calculation between two 1024 vectors.

Each damage monitoring unit 16 further comprises electrically conductive interconnections 32 that interconnect the electro-mechanical actuator 24, ignition element 26, sensors 28, and data collection device 30. Although FIG. 2 illustrates each damage monitoring unit 16 as including eight sensors 28, any number of sensors 28 may be utilized, including less than eight or greater than eight sensors 28. Likewise, additional nano-energetic actuators 22 and/or electro-mechanical actuators 24 may be utilized in the damage monitoring unit 16.

As one example, because each nano-energetic actuator 22 can only be used one time (i.e., once a nano-energetic actuator 22 is used to generate a controlled combustion, it cannot be used to generate another controlled combustion), multiple nano-energetic actuators 22 may be provided for each damage monitoring unit 16, so subsets of the nano-energetic actuators 22 can be activated over several NDEs. Preferably, the centroids of the subsets of the nano-energetic actuators 22 are at identical locations in order to mimic the same location from which the controlled combustion originates. As such, the acoustic signature generated by each subset from the perspective of the surrounding sensors 28 will be identical or near identical. If individual nano-energetic actuators 22 are activated or the centroids of sets of nano-energetic actuators are not the same, the different locations of the controlled combustions will have to be accounted for when comparing to a baseline.

Figure 3:
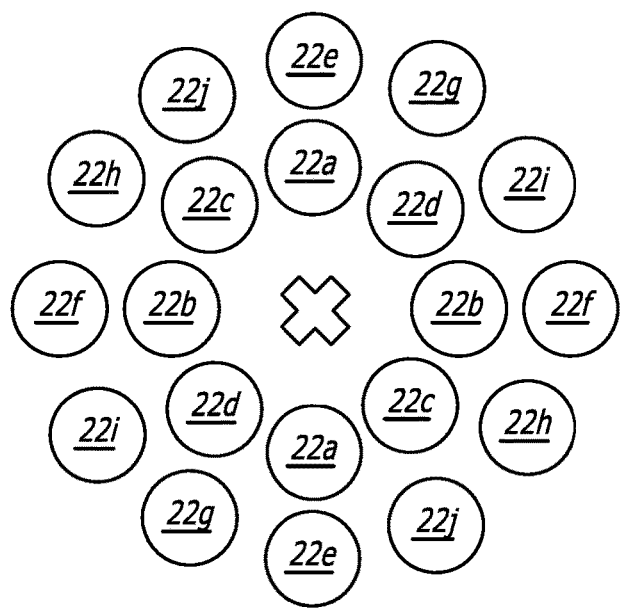
FIG. 3 is a plan view of nano-energetic actuators that can be incorporated in the NDE system of FIG. 2.

For example, with reference to FIG. 3, a "corral" of nano-energetic actuators 22 from which a subset of nano-energetic actuators 22 can be selected for activation for a particular NDE. As there shown, ten pairs of nano-energetic actuators 22a, 22b, 22c, 22d, 22e, 22f, 22g, 22h, 22i, and 22j can be respectively used for ten NDEs. Thus, actuators 22a can be activated for a first NDE, actuators 22b can be activated for a second NDE, actuators 22c can be activated for a third NDE, and so on. The centroid of each of these pairs of nano-energetic actuators 22 are located at the point "x," so that the actuators pairs have identical acoustic signatures relative to the sensors 28. It should be appreciated that the particular geometric arrangement of nano-energetic actuators 22 illustrated in FIG. 3 does not preclude other geometric arrangements of nano-energetic actuators 22 with uniform or non-uniform spacing or a totally random distribution of nano-energetic actuators 22. Furthermore, although the nano-energetic actuators 22 are illustrated in FIG. 3 as being of uniform size, the sizes of the nano-energetic actuators 22 may differ from each other to meet variable energy requirements for a given application.

Regardless of the number of nano-energetic actuators 22 contained in each damage monitoring unit 16, The CPD 18 is configuring for delivering trigger signals (e.g., electrical pulses or other signals (either directly or from a power source 20)) that activate the damage monitoring units 16 to generate vibrations in the respective structural elements 12, and for collecting data from the damage monitoring units 16. Thus, the CPD 18 controls the timing and performs data analysis to determine damage location and characteristics in each structural element 14. In order to activate a selected nano-energetic actuator 22 in one of the damage monitoring units 16, the CPD 18 sends a signal (e.g., a 5V pulse) via a trigger line 34 to the corresponding ignition element 26. In order to activate a selected electro-mechanical actuator 24, the CPD 18 may also send a signal via a trigger line 36 to electro-mechanical actuator 24. In one embodiment, the CPD 18 may also send a signal to the corresponding data collection device 30 for purposes of timing and to facilitate data collection. Further, the CPD 18 receives data from the data collection device 30 via the data line 38. While FIG. 2 shows the trigger lines 34, 36 and data line 38 as wired connections, the communications may be provided via wireless or other data transfer method. In addition, the trigger lines 34, 36 and the data line 38 may be a single wired connection or multiple wire connections.

Figure 4:
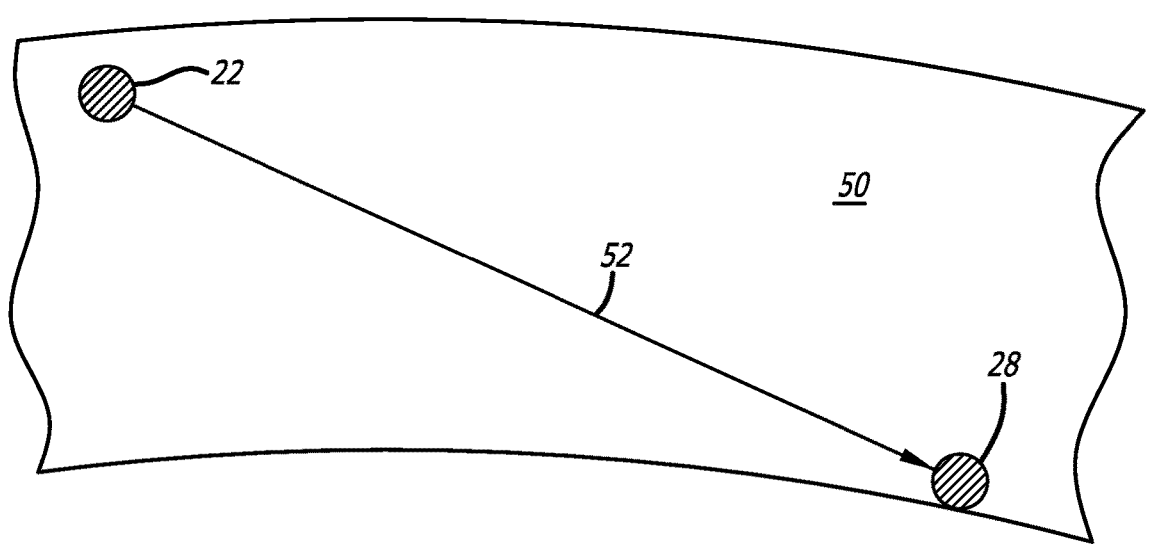
FIG. 4 is a plan view showing energy traveling along a path from a nano-energetic actuator to a sensor.

Referring further to FIG. 4, a single path arrangement between a nano-energetic actuator 22 (or optionally an electro-mechanical actuator 24) will now be described. The nano-energetic actuator 22 is activated (i.e., it creates a controlled combustion), such as by providing an electrical pulse to the corresponding ignition element 26. In response to the applied voltage, the controlled combustion generated by the nano-energetic actuator 22 induces a vibration in the surface of the structural element 12. The vibration propagates across the substrate 50 (representing the structural element 12) forming a vibratory path 52. The sensor 28 senses and measures vibration and/or movement corresponding to the vibration propagating along vibratory path 52. The sensor 28 generate a voltage in response to vibration. The voltage or a signal corresponding to the voltage can be transmitted to the data collection device 30 for collection and analyzing. Although the vibratory path 52 is illustrated as a single straight line, it is noted that the vibration generated by the nano-energetic actuator 22 propagates in all directions from the nano-energetic actuator 22 along the substrate 50, and thus, a plurality of vibratory paths 52 are present originating at the activated nano-energetic actuator 22.

In an alternative embodiment, multiple nano-energetic actuators 22 may be sequentially actuated, such that the controlled combustions are generated in a time-phased manner, thereby causing the vibrational energy to preferentially travel in a particular direction. In this case, the CPD 18 may transmit the trigger signals to the respective ignition elements 26 in a time-phased manner, or alternatively, differing signal delay elements (not shown) can be coupled to the ignition elements 26 via the respective electrically conductive interconnections 32, in which case, the CPD 18 may simultaneously transmit the trigger signals to the intervening signal delay elements.

In an optional embodiment, the vibration energy can be directed, focused reflected, filtered in frequency, or dispersed horizontally along the plane of the structural element 12 using surface acoustic wave structures. For example, raised lines can be printed on the structural element 12 to direct or reflect the vibrational energy. For example, such a surface acoustic wave structure may be placed in front of a component (e.g., a bolt) to prevent the vibrational energy from adversely affecting that component (e.g., loosening the bolt). As another example, a surface acoustic wave structure can be used to pass or reflect vibrational energy in a narrow frequency band towards a portion of the structural element 12 to be examined. Thus, surface acoustic wave structures can be used as a reflector or a filter to tune the direction and spectral content of energy entered in an area to be examined. As still another example, three surface acoustic wave structures can be constructed to reflect vibrational energy from a single controlled combustion from a nano-energetic actuator 22 into a "hidden" area (e.g., around a corner) of the structural element 12, thereby emulating three separate but simultaneous controlled combustions.

Regardless of the nature of the vibrational energy, each data collection device 30 receives the data from the sensors 28 and calculates a damage index (DI) value corresponding to the data obtained. In particular, the data collection device 30 compares data obtained from sensors 28 to data previously collected from sensors 28 on the undamaged structural element 12. Specifically, while not so limited, the data collection device 30 may perform the following calculation to determine a root mean square value damage index (DI) value, as follows:

$$DI = \frac{\text{RMS}(Data_{cur} - Data_{ref})}{\text{RMS}(Data_{ref})},$$

where $Data_{cur}$ corresponds to current data (e.g., a vector of 1024 elements corresponding to measured voltages) obtained from sensors 28; and $Data_{ref}$ corresponds to previous (baseline) data obtained from the sensors 28 when the respective structural element 12 is known to be in an undamaged condition. The DI value computed by the data collection device 30 may be transmitted to and used by the CPD 18 to determine the location and/or nature of any damage that is present in the respective structural element 12.

In one embodiment, DI includes eight scalar answers or responses (one per channel or one per sensor 28) that are returned to the corresponding data collection device 30, which are then transmitted to and used by the CPD 18 to determine the location and/or nature of any damage that is present in the corresponding structural element 12. While the calculation shown above is a root mean square calculation, other data manipulation, algorithms or calculations may be utilized, as desired, to obtain DI values that are able to determine the location and character of damage on the structural element 12.

In the embodiments including adjacent damage monitoring units 16, the nano-energetic actuators 22 and/or optional electro-mechanical actuators 24 are activated in a manner that minimizes vibration interference at the individual sensors 28. In other words, for any particular damage monitoring unit 16, the lengths of the vibratory paths 52 between the actuators 22/24 generating the vibration and the sensors 28 measuring the vibrations are maintained, such that the vibrations at sensors 28 are substantially free of vibrations (i.e., amplitude at the vibration is sufficiently small) generated by actuators 22/24 in other damage monitoring units 16.

Figure 5:
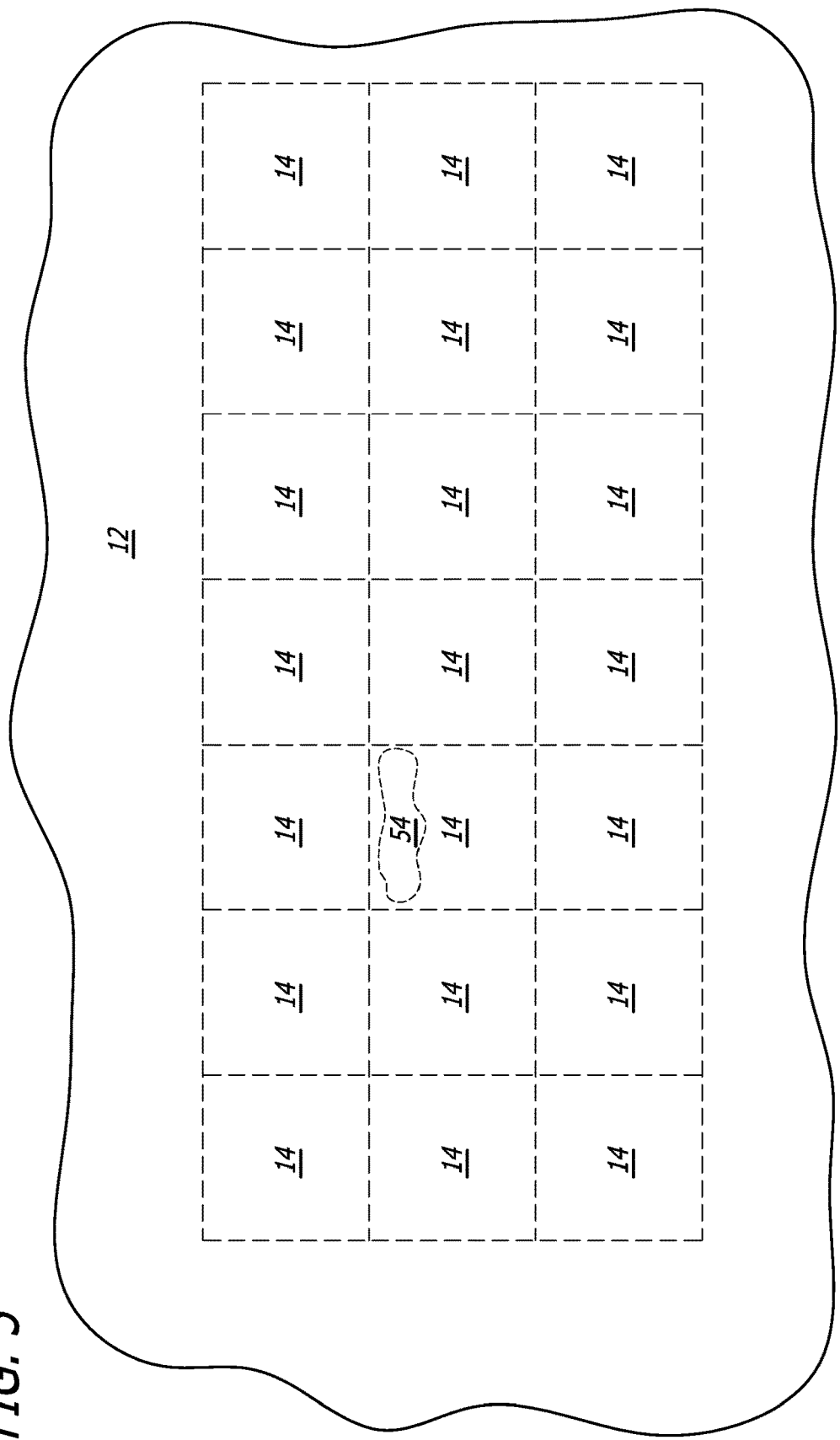
FIG. 5 is an array of damage monitoring units of the NDE system of FIG. 2 that can be used to identify and locate a damaged area in the structural element.

Furthermore, although only one damage monitoring unit 16 is illustrated in FIG. 1 as being associated with each structural element 12, multiple damage monitoring units 16 may be arranged over a large area of the respective structural element 12 in order to obtain high resolution health monitoring, as illustrated in FIG. 5. In this case, for each structural element 12 to be examined, the damage monitoring units 16 are arranged and preferably activated at periodic intervals to monitor the health of the respective structural element 12. Alternatively, the damage monitoring units 16 may be activated at the same time, provided that the activated damage monitoring units 16 are sufficiently spaced to permit the vibration amplitude to sufficiently decay to reduce or eliminate undesired noise at the sensors 28 of activated adjacent damage monitoring units 16.

As shown in FIG. 5, an area of damage 54 is present on the structural element 12, which may have been caused by impact, contact, abrasion or any other type of contact that may result in scratching, delamination or other damage that may affect the mechanical or other properties of the structural element 12. One of the damage monitoring units 16 spans this damaged area 54. Although FIG. 5 illustrates he damaged area 54 as being spanned by only one damage monitoring unit 16, it should be appreciated that the damaged area 54 may coincide with several damage monitoring units 16.

Figure 6:
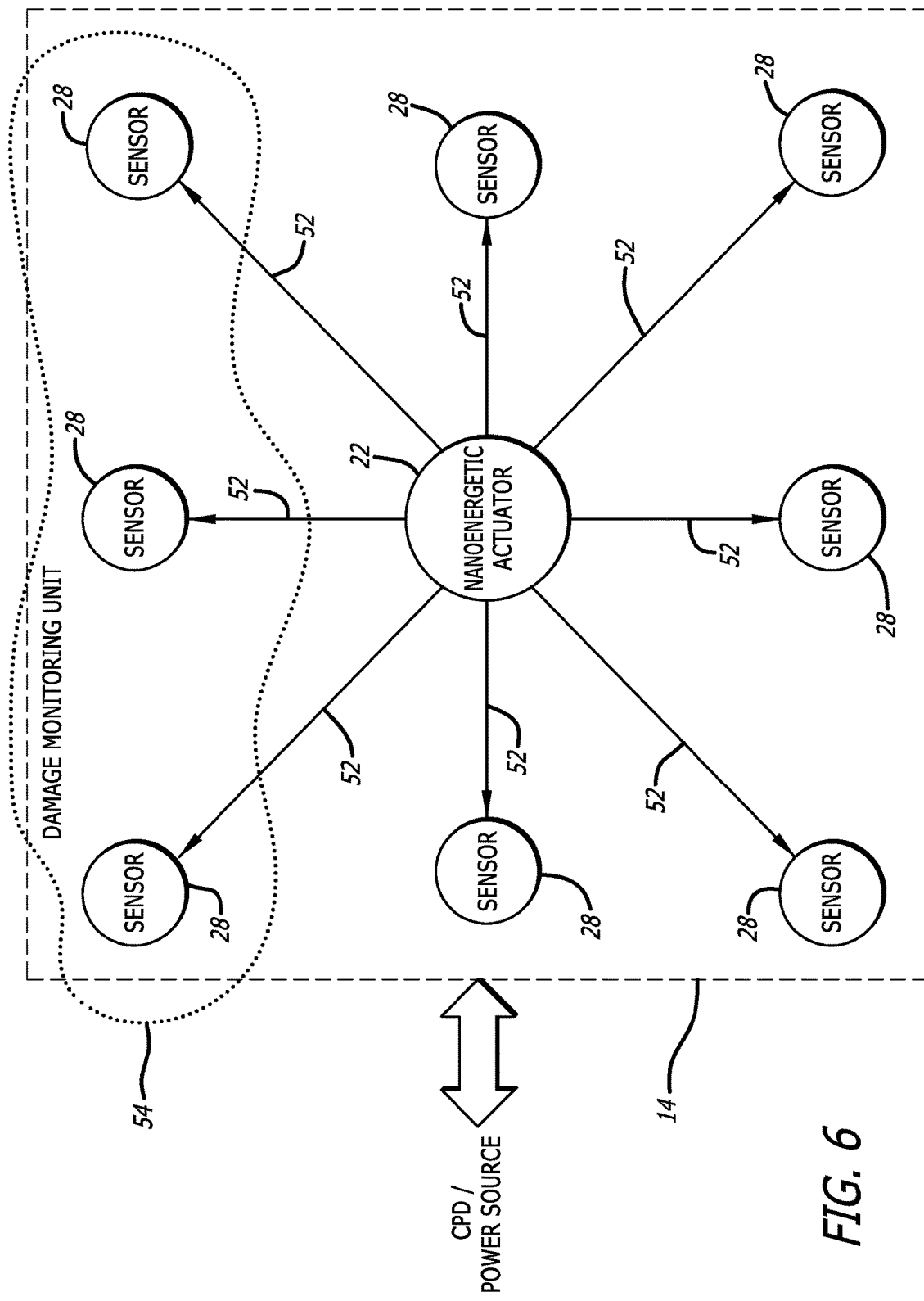
FIG. 6 is a block diagram of one damage monitoring unit of the array of damage monitoring units of FIG. 5, wherein the damage monitoring unit is adjacent a damaged area of the structural element.

As shown in FIG. 6, this damage monitoring unit 16 during the process of monitoring the health of the structural element 12 taken from damaged area 54 of FIG. 5 will now be described. A signal from the CPD 18 (not shown in FIG. 6) is provided to the ignition element 26 of the nano-energetic actuator 22 and the data collection device 30 (not shown in FIG. 6) to activate the nano-energetic actuator 22 and to optionally prepare the data collection device 30 (not shown in FIG. 6) to receive data. In response, the nano-energetic actuator 22 generates a controlled combustion that induces a vibration that propagates across the surface of the structural element 12 and along vibratory paths 52. The vibratory paths 52 travel across the structural element 12 and may be measured by the sensors 28. The sensors 28 transmit the measured vibration to the data collection device 30, which obtains and analyzes the data.

In one embodiment, the data collection device 30 compares the voltages transmitted by the sensors 28 to a stored set of data corresponding to an undamaged structural element 12. If the structural element 12 is substantially undamaged, the voltages measured and the voltages stored are substantially the same and the resultant DI is zero or about zero. However, if damage is present as represented by the damaged area 54, the sensors 28 within the damaged area 54 will measure a level of vibration different than the vibration measured on an undamaged structural element 12, and therefore can characterize and locate the damaged area 54. In the example shown in FIG. 5, the three sensors 28 within the damaged area 54 will return a value of DI that is non-zero, while the remaining five sensors 28 outside of the damaged area will return a DI of substantially zero. Additional factors such as magnitude of the DI may also be utilized to characterize the damaged area 54. The DIs calculated by the data collection device 30 are transmitted to the CPD 18, wherein a plurality of damage monitoring units 16 also transmit the DIs in order to provide data that can determine the location and characterization of the damaged area 54. The characterization of damage may include the size, depth type or other feature of the damage.

The nano-energetic actuators 22, optional electro-mechanical actuators 24, ignition elements 26, sensors 28, and data collection device 30 may be affixed to the structural element 12 in any suitable manner that permits the generation of vibration in the structural element 12 by the nano-energetic actuators 22 and optional electro-mechanical actuators 24 and the measurement of vibration of the sensors 28.

For example, the nano-energetic actuators 22, ignition elements 26, and associated electrically conductive interconnections 32 may be directly deposited on an exterior surface of the structural element 12 using any suitable printing or lithography technique. The optional electro-mechanical actuators 24 and sensors 28 may be deposited on an interior surface of the structural element 12 (e.g., the interior surfaces of the fuselage of an aircraft) using any suitable printing or lithography technique, wherein the exposure to damage to these components would otherwise be on an exterior surface. As one example, components that take the form of PZTs (e.g., the electro-mechanical actuators 24 and sensors 28) can be deposited directly onto a structural element 12 by a method such as, but not limited to fused deposition of ceramics, robocasting, micropen application, sintering onto the surface using light energy from a high energy source, such as a laser or a xenon flash lamp, or any other suitable PZT deposition process. One suitable method includes the direct sintering and using laser based sintering techniques recited in U.S. Pat. No. 6,531,191, which is expressly incorporated herein by reference.

The data collection device 30 may be soldered, attached, formed or otherwise disposed on the structural element 12 and interconnected to the electro-mechanical actuators 24 and sensors 28 via the electrically conductive interconnections 32, which may be applied using any known application and/or conductive trace printing technique, including, but not limited to direct printing or lithographic methods. The CPD 18 may be incorporated into any region of the vehicle 10 and wired to the damage monitoring units 16.

Figure 7:
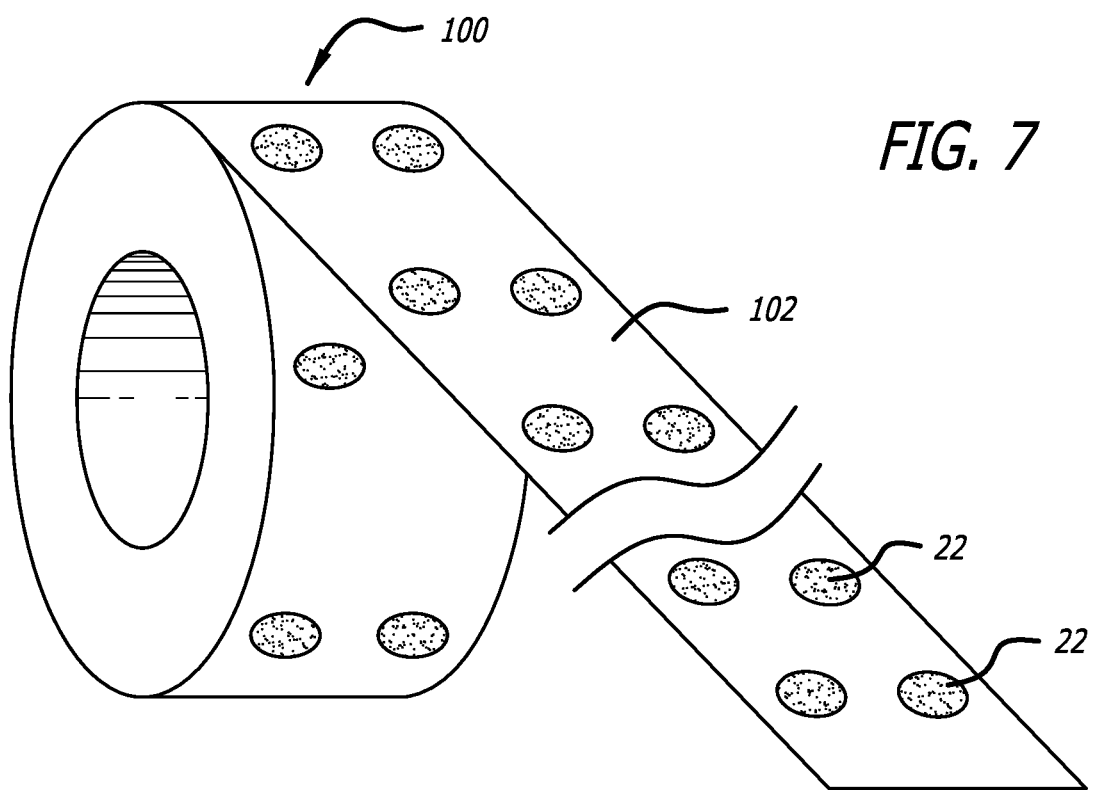
FIG. 7 is a perspective view of an applique constructed in accordance with one embodiment of the present inventions for use in the NDE system of FIG. 2.
Figure 8:
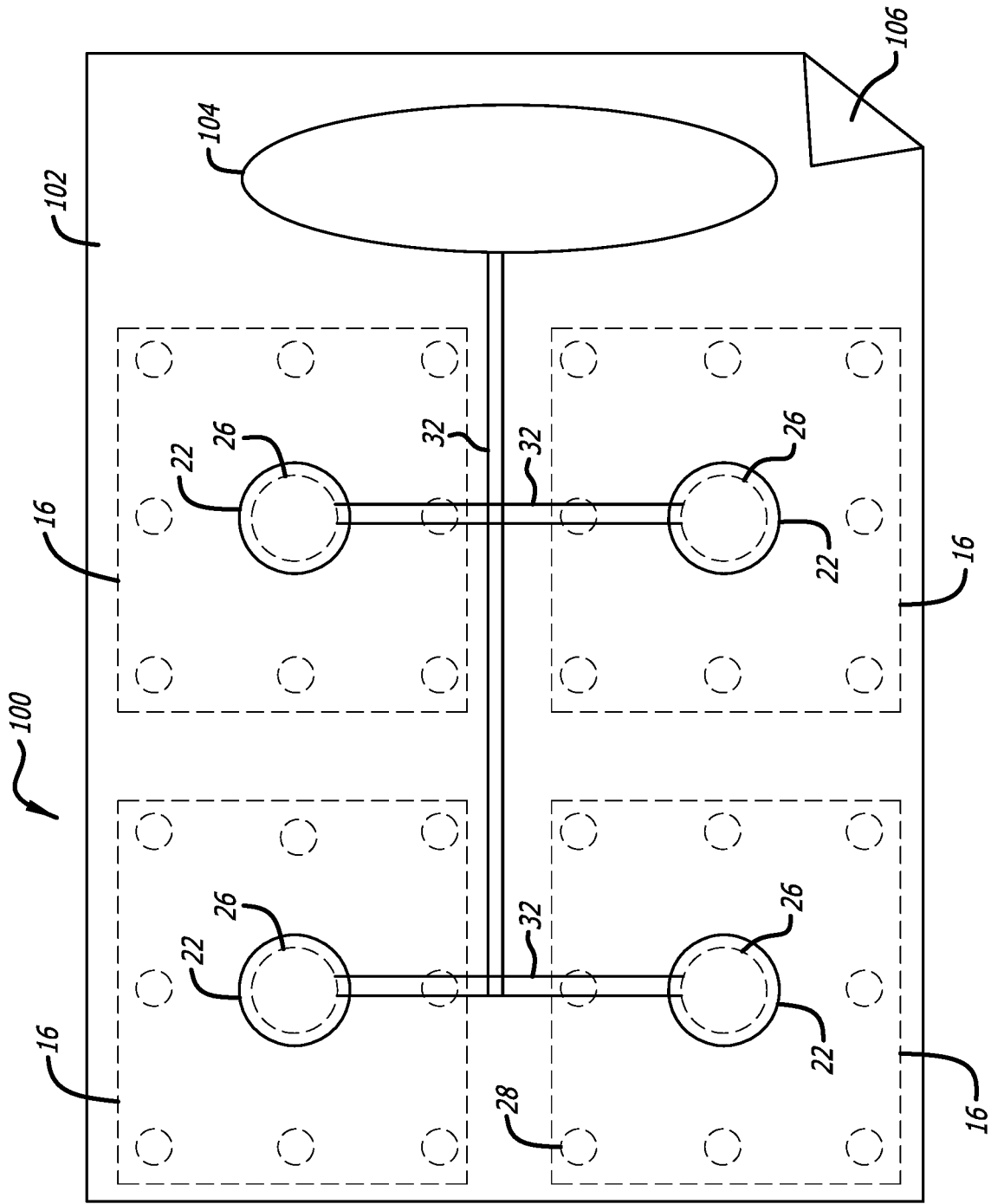
FIG. 8 is a plan view of the applique of FIG. 7.

In one particularly advantageous embodiment, the nano-energetic actuators 22, ignition elements 26, and associated electrically conductive interconnections 32 may be provided in sheet form as an applique 100 that can be semi-permanently or temporarily affixed to the external surface of the structural element 12, as illustrated in FIGS. 7 and 8. In the illustrated embodiment, the applique 100 is supplied in the form of a roll (shown in FIG. 7) from which adjustable lengths of the applique 100 can be ripped or cut. Thus, the applique 100 may permit reusability and/or portability of the actuation portion of the NDE system 14. For example, the applique 100 can be designed for being single-use only, such that after the NDE is performed, the used applique 100 can be removed, and replaced with an identical applique 100 for immediate or subsequent use.

To this end, the applique 100 comprises a flexible planar substrate 102 (such as a polymeric material, e.g., polyimide film (e.g., Kapton®), metallic foil, a metalized polymeric material, or a multilayer substrate of polymeric and metallic films) on which the plurality of the nano-energetic actuators 22, ignition elements 26, and electrically conductive interconnections 32 are affixed to one side using a suitable process, e.g., printing or lithography. The ignition elements 26 are thermally coupled to the nano-energetic actuators 22, and in the illustrated embodiment, are disposed between the planar substrate 102 and nano-energetic actuators 22. The electrically conductive interconnections 32 are electrically coupled to the ignition elements 26. Thus, triggering signals may be input onto the ignition elements 26 via the electrically conductive interconnections 32, thereby activating the nano-energetic actuators 22 to generate controlled combustions. If multiple nano-energetic actuators 22 are activated in a time-phased manner to control the direction of the vibrational energy along the structural element 12, delay elements (not shown) may be incorporated into the electrically conductive interconnections 32 and affixed to the planar substrate 102.

It should be appreciated that, in addition to providing a means for integrating the applique 100, the planar substrate 102 provides a protective barrier between the controlled combustions generated by the nano-energetic actuators 22 and the structural element 12. In a contrasting embodiment, the planar substrate 102 may serve as a stiff backing plate (instead of a protective barrier) to vertically direct the vibrational energy into the structural element 12. As will be described in further detail below, the applique 100 may be used in de-icing procedures, in which case, the planar substrate 102 may be used to vertically direct the energy outward. In any event, the applique 100 may further comprise a conformal polymer coating (not shown) disposed over the components to protect them from environmental conditions. Further, this protective coating would be designed to address any barrier requirements related to moisture, oxygen, etc. As such, this protective coating may, e.g., take the form of a multi-layer barrier film. In the extreme, this protective material could be sufficient to add its own mechanical properties to the structure to require consideration in the analysis of the data produced, e.g., one or more layers of fiberglass or carbon fiber based polymer composites.

To provide a communication/power means for the applique 100, the applique 100 further comprises at least one inductive coil 104 (only one shown) affixed to the substrate 102. The inductive coil 104 is configured for receiving trigger signals from a corresponding inductive coil (not shown) associated with the CPD 18. The inductive coil 104 is electrically coupled to the ignition elements 26 via the electrically conductive interconnections 32, such that trigger signals received by the inductive coil 104 actuate the nano-energetic actuators 22. As such, the applique 100, when applied to the structural element 12, need not be hardwired to the CPD 18. Alternatively, the applique 100 may be hardwired to the CPD 18, such that the inductive coil 104 is not needed. In this case, the applique 100 may have exterior wires or electrical pads that can be used to electrically connect its components to remaining circuitry of the NDE system 14. In another alternative embodiment, a photo cell may be provided on the applique 100, and an optical source (e.g., a lase or even the Sun) may emit light onto the photocell, which can be used as power/communication after conversion to electricity. In still another embodiment, an energy storage device, such as a battery, may be provided on the applique 100 for providing power/communication to the applique 100.

In one embodiment, the nano-energetic actuators 22 are registered to the centers of the damage monitoring units 16, with the sensors 28 (shown in phantom), and the other componentry being affixed directly to the surface element 12 underneath the applique 100. For example, if the damage monitoring units 16 are spaced six inches apart, the nano-energetic actuators 22 may be likewise spaced six inches apart. Thus, when adhering the applique 100 to the structural element 12, the nano-energetic actuators 22 may be aligned with the centers of the damage monitoring units 16.

Although the electro-mechanical actuators 24, sensors 28, and data collection devices 30 have been described as being directly affixed to or in the structural element 12 separately from the applique 100, it should be appreciated that the electro-mechanical actuators 24, sensors 28, and/or data collection devices 30 may be affixed to the planar substrate 102 using any suitable means. However, because the electro-mechanical actuators 24, sensors 28, and/or data collection devices 30 are generally reusable, they can easily be incorporated into the structural element 12, and thus, for purposes of efficiency in manufacture and associated cost, these devices may advantageously be incorporated into the structural element 12.

The applique 100 further comprises an adhesive 106 affixed to the planar substrate 102, such that the applique 100 can be adhered to the structural element 12. In one preferred embodiment, the adhesive 106 is such that the applique 100 can be easily removed from the structural element 10 after a single use. Such an applique 100 is quite useful when used on structural elements 12 that are easily accessible. The side of the planar substrate 102 on which the adhesive 106 is applied may depend on the particular use of the applique 100. For NDE, the adhesive 106 may be applied to the same side of the planar substrate 102 on which the nano-energetic actuators 22 are disposed. In this case, when the applique 100 is adhered to the structural element 12, the nano-energetic actuators 22 will be facing the structural element 12, such that the planar substrate 102 directs the energy from the controlled combustions towards the structural element 12. For de-icing procedures if the vehicle 10 is an aircraft, as will be described in further detail below, the adhesive 106 may be applied to the side of the planar substrate 102 opposite to the side on which the nano-energetic actuators 22 are disposed. In this case, when the applique 100 is adhered to the wings or flight control surfaces (e.g., flaps, ailerons, elevators, rudders of the aircraft 10, the nano-energetic actuators 22 will be facing outward away from the wings or flight control surfaces, such that the planar substrate 102, while also creating a barrier between the energy created by the controlled combustions, directs such controlled combustions outwards towards the ice.

In an alternative embodiment, the adhesive 106 is such that the applique 100 is semi-permanently affixed to the structural element 10 for multiple uses. In this case, multiple nano-energetic actuators 22 are provided for each damage monitoring unit 16. For each NDE performed, one set of nano-energetic actuators 22 will be activated and therefore used up. Preferably, the applique 100 in this case will have enough nano-energetic actuators 22 to support several NDEs performed over a period of time, e.g., as shown in FIG. 3. Such a reusable applique 100 can be applied to a structural element 12 in an inaccessible location of the vehicle 10, e.g., during manufacture of the vehicle 10. As one example, if such structural element 12 will not be accessed for a period of time (e.g., 10 years), the reusable applique 100 may have enough nano-energetic actuators 22 for each damage monitoring unit 12 to last for all anticipated NDEs during this period of time.

Figure 9:
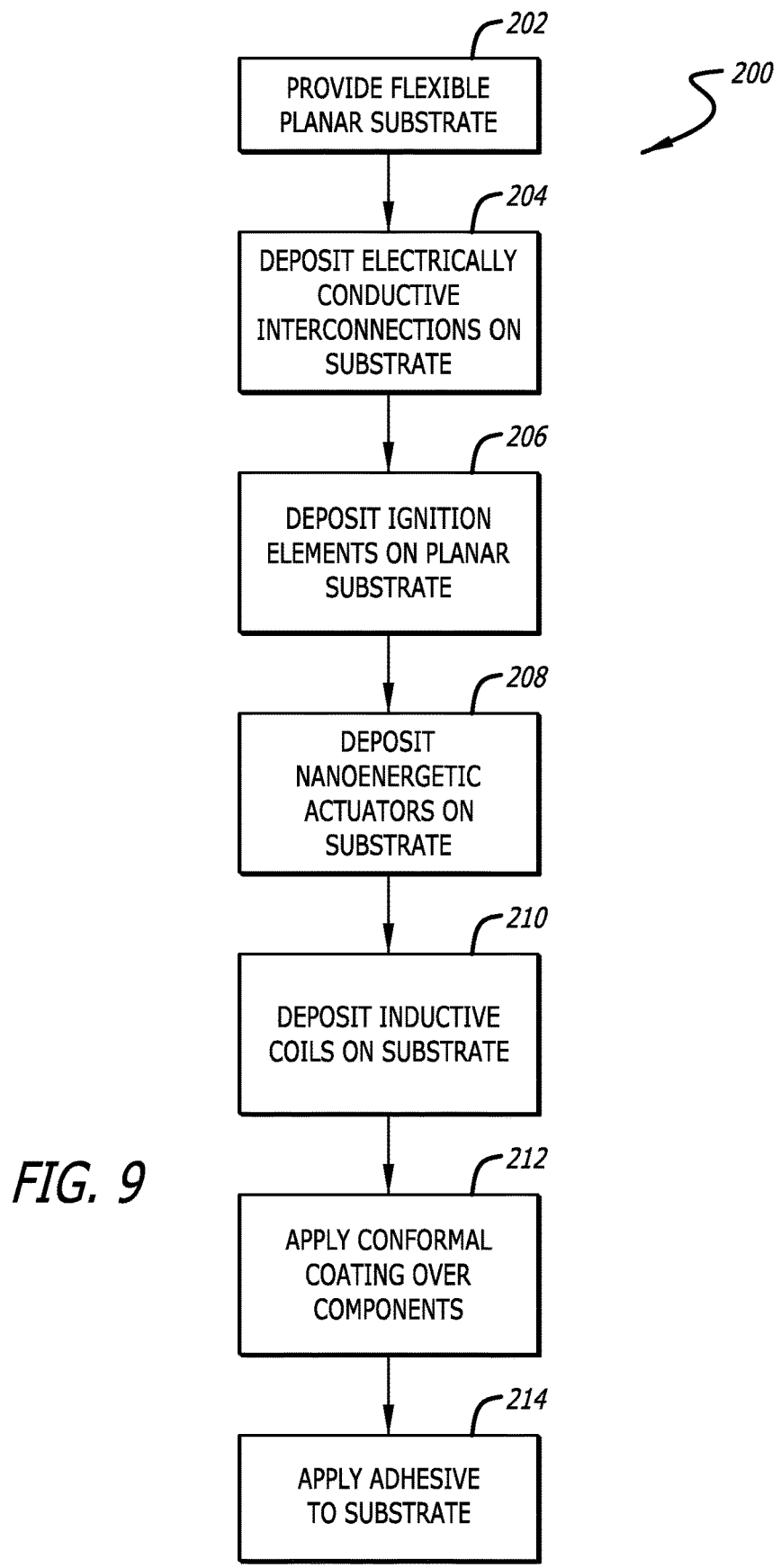
FIG. 9 is a flow diagram illustrating one method of manufacturing the applique of FIGS. 7 and 8.

Referring to FIG. 9, one method 200 of manufacturing the applique 100 will now be discussed. First, the flexible planar substrate 102 (e.g., polyimide) is provided (step 202). The electrically conductive interconnections 32 (step 204) and ignition elements 26 (step 206) are deposited on the planar substrate 102, e.g., via printing or lithography, such that the electrically conductive interconnections 32 and ignition elements 26 are electrically coupled together. Next, the nano-energetic actuators 22 are deposited on the planar substrate 102, so that they are thermally coupled to the ignition elements 26, and in the illustrated embodiment, respectively on the ignition elements 26 (step 208).

Next, the inductive coil(s) 104 are deposited on the planar substrate 102, such that they are electrically coupled to the ignition elements 26, and in the illustrated embodiment, on the electrically conductive interconnections 32 (step 210). Optionally, a conformal coating may be applied over the components (step 212).

Lastly, an adhesive is applied to the planar substrate 102 (step 214). In one embodiment, the adhesive is applied to the same side of the planar substrate 102 as the nano-energetic actuators 22, so that the energy from the subsequent controlled combustions is directed away from the planar substrate 102 toward structural element 12. The characteristics of the adhesive may be selected, not just for addressing adhesion requirements, but also to address any impedance matching requirements. This may be useful, e.g., when performing NDE on the structural element 12. In another embodiment, the adhesive is applied to the opposite side of the planar substrate 102 as the nano-energetic actuators 22, so that the energy from the subsequent controlled combustions is directed outward away from the planar substrate 102. This may be useful, e.g., when performing a de-icing procedure.

Figure 10:
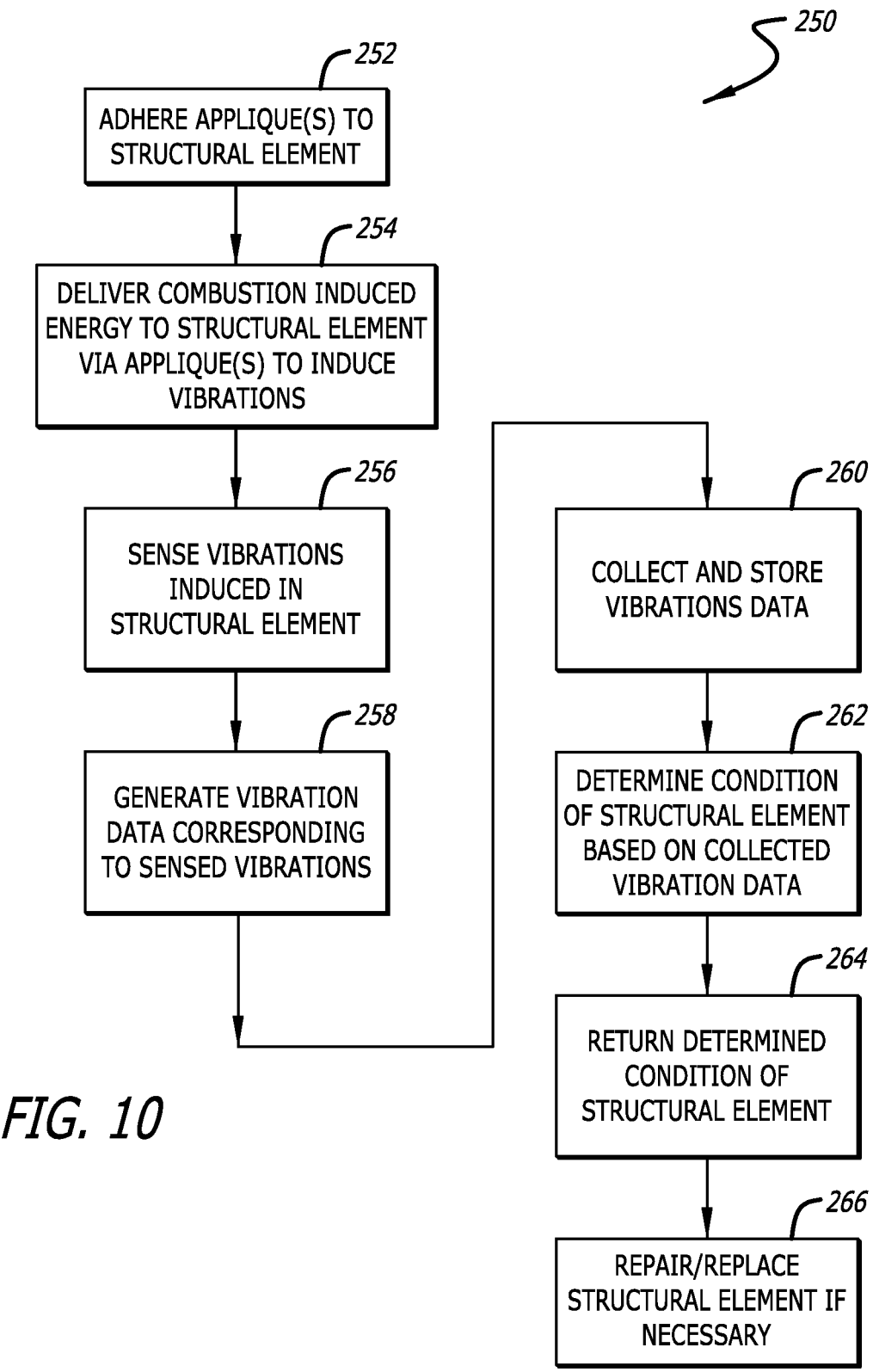
FIG. 10 is a flow diagram illustrating one method of operating the NDE system of FIG. 2 with the applique of FIGS. 7 and 8 to identify and locate damage in a structural element.

Having described the function and arrangement of the NDE system 14, one method 250 of operating the NDE system 14 to perform an NDE on a structural element 12 of the vehicle 10 will now be described with respect to FIG. 10. In this example, the NDE system 14 utilizes one or more appliques 100 that complement the sensors 28, data collection devices 30, and associated circuitry of one or more damage monitoring units 12 that have been previously integrated with the structural element 12. Performance of the NDE on the structural element 12 can be performed using a single damage monitoring unit 16 or multiple damage monitoring units 16.

First, one or more appliques 100 are adhered to the structural element 12, such that the nano-energetic actuators 22 of the applique(s) 100 are in registration with the portions of the damage monitoring units 16 (e.g., the sensors 28 and data collection devices 30) that have been directly incorporated into the structural element 12, itself (step 252). Combustion induced energy is then delivered to the structural element 12 via the applique(s) 100, thereby inducting vibrations in the structural element 12 (step 254). In the illustrated embodiment, this is accomplished by sending at least one trigger signal from the CPD 18 to the ignition element(s) 26 to activate the respective nano-energetic actuators 22 carried by the applique 100. Multiple controlled combustions may be applied to the structural element 12 in a time-phased manner to preferentially induce the vibrations along a particular direction in the structural element 12.

In an alternative embodiment, vibrations are induced in the structural element 12 via actuation of the electro-mechanical actuators 24 if a relatively large amount of vibrational energy is not needed to perform the NDE of the structural element 12. In this manner, unnecessary use of the nano-energetic actuators 22 may be avoided, thereby increasing the useful life of the applique 100. Thus, the nano-energetic actuators 22 will only be actuated if the NDE of the structural element 12 cannot be accurately performed using the electro-mechanical actuators 24, alone. Next, the vibrations induced in the structural element 12 are sensed (step 256), and vibration data corresponding to the measured vibrations is generated by the sensors 28 integrated into the structural element 12 (step 258). Then, the vibration data is collected from the individual sensors 28 and stored by the data collection device 30 (step 260).

Then, the condition of the structural element 12 is determined based on the collected and stored vibration data (step 262). In the illustrated embodiment, the data collection device(s) 30 integrated into the structural element 12 compares vibration data collected from each sensor 28 and compares it to reference vibration data, e.g., to obtain a DI for each sensor 28. It may be determined that the structural element 12 has damage or deterioration in any region adjacent any sensors 28 returning a non-zero DI. If all sensors 28 return a DI that is substantially non-zero, the structural element 12 will be deemed to be free from damage or deterioration. Then, the determined condition of the structural element 12 is returned to the CPD 18 (step 264). Lastly, the structural element 12 is repaired or replaced if it is determined that the structural element 12 has been damaged or has deteriorated (step 266).

Although the applique 100 has been described as being used to facilitate NDE of a vehicle, it should be appreciated that the use of an applique 100 lends itself well to the performance of NDEs on fixed structures, such as bridges, railways, and buildings. In a conventional scenario, a huge amount of time is typically expended in the setting up and tearing down of NDE equipment in the inspection of these structures. Appliques 100 may be conveniently affixed to these structures (e.g., at every major intersection of metal where rust may form), which may substantially reduce the set up and tear down time.

Although the nano-energetic actuators 22 have been described as being used in the context of performing NDEs on structural elements 12, nano-energetic actuators 22 may be used in the context of a de-icing system as briefly discussed above. In this case, nano-energetic actuators 22 and associated ignition elements 26, as well as electro-mechanical actuators 24, may be incorporated into the vehicle 10, in this case an aircraft, for example, on the wings or flight control surfaces of aircraft 10. Notably, the sensors 28 and data collection devices 30 are not required in this de-icing system. The CPD 18 transmits trigger signals to the ignition elements 26 associated with the nano-energetic actuators 22 and the electro-mechanical actuators 24 in a manner that effectively and efficiently removes the build-up of ice on the wings or flight control surfaces of the aircraft 10, even if such ice is too thick to be quickly removed using conventional means. In particular, the CPD 18 may transmit trigger signals to the ignition elements 26, thereby activating the corresponding the nano-energetic actuators 22 to generate controlled combustions that induce vibrations in the ice great enough to generate cracks in the ice. The CPD 18 may also transmit trigger signals to the electro-mechanical actuators 24, thereby activating the electro-mechanical actuators 24 to generate vibrations in the ice great enough to remove the cracked ice from the wings or flight control surfaces of the aircraft 10.

Figure 11:
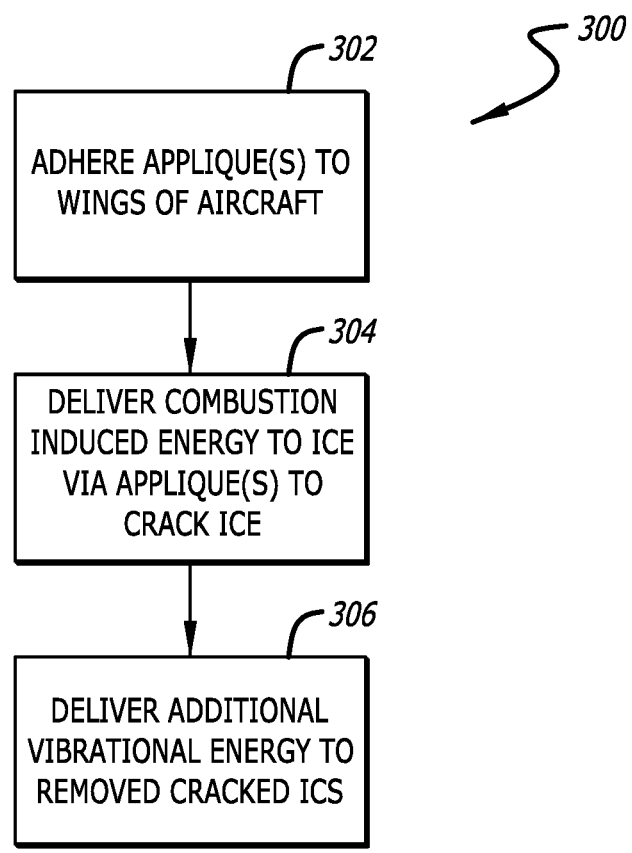
FIG. 11 is a flow diagram illustrating one method of operating a de-icing system with the applique of FIGS. 7 and 8 to remove ice from the wings or flight control surfaces of an aircraft.

Referring now to FIG. 11, one method 300 of using an applique 100 in a de-icing procedure performed on a structure, such as a vehicle 10, will now be described. In this example, the appliques 100 complement the electro-mechanical actuators 24 that have previously integrated with the vehicle 10. In an alternative embodiment, the applique 100 can be used in the de-icing procedure without electro-mechanical actuators 24.

First, appliques 100 are adhered to the wings or flight control surfaces of the aircraft 10 over the electro-mechanical actuators 24 that have been directly incorporated into the wings or flight control surfaces of the aircraft 10 (step 302). Combustion induced energy is then delivered to the ice on the wings or flight control surfaces of the aircraft 10 via appliques 100, thereby inducing vibrations that crack the ice (step 304). In the illustrated embodiment, this is accomplished by sending at least one trigger signal from the CPD 18 to the ignition elements 26 to activate the respective nano-energetic actuators 22 carried by the applique 100. Multiple controlled combustions may be applied to the structural element 12 in a time-phased manner to preferentially induce the vibrations along a particular direction. Then, additional vibrational energy is applied to the cracked ice, thereby removing the cracked ice from the wings or flight control surfaces of the aircraft 10 (step 306). In the illustrated embodiment, this is accomplished by sending at least one trigger signal from the CPD 18 to the electro-mechanical actuators 24. In an alternative embodiment, the vibrational energy may be applied to the ice via the electro-mechanical actuators 24 prior to activation of the nano-energy actuators 22 in an attempt to remove the ice from the wings or flight control surfaces of the aircraft 10 using the electro-mechanical actuators 24, alone. In this manner, unnecessary use of the nano-energetic actuators 22 may be avoided, thereby increasing the useful life of the applique 100. Thus, the nano-energetic actuators 22 will only be actuated if the ice cannot be removed from the wings or flight control surfaces using the electro-mechanical actuators 24, alone.

Although certain illustrative embodiments and methods have been disclosed herein, it can be apparent from the foregoing disclosure to those skilled in the art that variations and modifications of such embodiments and methods can be made without departing from the true spirit and scope of the art disclosed. Many other examples of the art disclosed exist, each differing from others in matters of detail only. Accordingly, it is intended that the art disclosed shall be limited only to the extent required by the appended claims and the rules and principles of applicable law.

We claim:

1. A non-destructive examination (NDE) system for use on a structural element, comprising:
at least one ignition element configured for generating thermal energy;
at least one nano-energetic actuator, each configured for creating a controlled combustion in response to the thermal energy, thereby inducing vibrations in a surface of the structural element; and
at least one sensor configured for measuring the vibrations induced in the surface of the structural element and generating vibration data.

2. The NDE system of claim 1, further comprising a data collection device configured for collecting and storing the vibration data.

3. The NDE system of claim 2, further comprising at least one processor configured for determining a condition of the structural element based on the collected and stored vibration data.

4. The NDE system of claim 1, wherein the at least one nano-energetic actuator comprises a plurality of nano-energetic actuators, the NDE system further comprising at least one processor programmed to control delivery of a plurality of electrical pulses from the at least one electrical source to cause the plurality of nano-energetic actuators to generate a plurality of controlled combustions in a time-phased manner.

5. The NDE system of claim 1, further comprising at least one electro-mechanical actuator, each configured for vibrating in response to at least one electrical pulse, thereby inducing vibrations in the surface of the structural element.

6. The NDE system of claim 1, wherein each of the at least one nano-energetic actuator comprises nano-energetic material having a particle size less than one hundred nanometers.

7. The NDE system of claim 1, wherein each of the at least one nano-energetic actuator has a size in the range of one micrometer to four millimeters.

8. The NDE system of claim 1, further comprising:
at least one energy source configured for generating at least one electrical pulse,
wherein the at least one ignition element is further configured to generate the thermal energy in response to the at least one electrical pulse.

9. The NDE system of claim 8, wherein each of the at least one nano-energetic actuator comprises copper oxide, and each of the at least one ignition element comprises platinum.

10. A means of transportation, comprising: a structural element; and the NDE system of claim 1 mounted to the structural element.

11. The means of transportation of claim 10, wherein the structural element is one of a structural element of a bridge and a railroad.

12. The means of transportation of claim 10, wherein the structural element is a vehicular structural element.

13. The means of transportation of claim 12, wherein the structural element is an aircraft structural element.

14. A method of performing a non-destructive examination (NDE) on a structural element, comprising:
   generating, by at least one ignition element, thermal energy;
   applying, by at least one nano-energetic actuator, at least one controlled combustion, in response to the thermal energy, to the structural element, thereby inducing vibrations in the structural element;
   measuring the vibrations induced in the surface of the structural element;
   generating vibration data corresponding the measured vibrations;
   collecting and storing the vibration data; and
   determining a condition of the structural element based on the collected and stored vibration data.

15. The method of claim 14, wherein the at least one controlled combustion does not damage the structural element.

16. The method of claim 14, wherein the at least one controlled combustion comprises a plurality of controlled combustions, and wherein the plurality of controlled combustions is applied to the structural element in a time-phased manner to preferentially induce the vibrations along a particular direction in the structural element.

17. The method of claim 14, wherein the structural element is used in a transportation means.

18. The method of claim 17, wherein the structural element is used in one of a bridge and a railroad.

19. The method of claim 18, wherein the structural element is a vehicular structural element.

20. The method of claim 19, wherein the structural element is an aircraft structural element.

21. The method of claim 20, wherein the at least one controlled combustion is applied to the aircraft structural element in-flight.

* * * * *